United States Patent [19]
Fire et al.

[11] Patent Number: 5,648,245
[45] Date of Patent: Jul. 15, 1997

[54] METHOD FOR CONSTRUCTING AN OLIGONUCLEOTIDE CONCATAMER LIBRARY BY ROLLING CIRCLE REPLICATION

[75] Inventors: Andrew Fire; Si-Qun Xu, both of Baltimore, Md.

[73] Assignee: Carnegie Institution of Washington, Washington, D.C.

[21] Appl. No.: 437,538

[22] Filed: May 9, 1995

[51] Int. Cl.$^6$ .......................... C12P 19/34; C12N 15/64; C12N 15/66
[52] U.S. Cl. ....................... 435/91.1; 435/91.4; 435/91.41
[58] Field of Search ................................ 435/91.1, 91.4, 435/91.41

[56] References Cited

U.S. PATENT DOCUMENTS 5,426,180  6/1995  Kool ........................................ 536/25.3
5,478,731  12/1995  Short ....................................... 435/91.4

OTHER PUBLICATIONS

Koo, et al., "Determination of the Extent of DNA Bending by an Adenine–Thymine Tract", Biochemistry, 1990, pp. 4227–4234.

Jürgen Engel, "Laminins and Other Strange Proteins", Biochemistry, vol. 31, No. 44, Nov. 10, 1992, pp. 10643–10651.

Bartel, et al., "Isolation of New Ribozymes from a Large Pool of Random Sequences", Science, vol. 261, Sep. 10, 1993, pp. 1411–1418.

Beutel, et al., "In Vitro Evolution of Intrinsically Bent DNA", J. Mol. Biol. 1992 228, pp. 803–812.

Barbas, III, et al. "Selection of Human Anti–Hapten Antibodies from Semisynthetic Libraries", Gene, 137, 1993, pp. 57–62.

Vergnaud, et al., "The Use of Synthetic Tandem Repeats to Isolate New Vntr Loci: Cloning of a Human Hypermutable Sequence", Genomics 11, 1991, pp. 135–144.

*Primary Examiner*—David Guzo
*Assistant Examiner*—Thanda Wai
*Attorney, Agent, or Firm*—Cushman Darby & Cushman, L.L.P.

[57] ABSTRACT

An in vitro method for constructing an oligonucleotide concatamer library is revealed. The method has four steps. The first step involves the generation of a primer-bridged circular template oligonucleotide. In the second step, the primer-bridged circular template is used to generate a single-stranded oligonucleotide concatamer by rolling circle replication. In the third step, the single-stranded oligonucleotide concatamer is converted to a double-stranded oligonucleotide concatamer. Finally, the double-stranded oligonucleotide concatamer is cloned or used directly in in vitro assays which allow molecules of interest to be isolated or amplified.

9 Claims, 8 Drawing Sheets

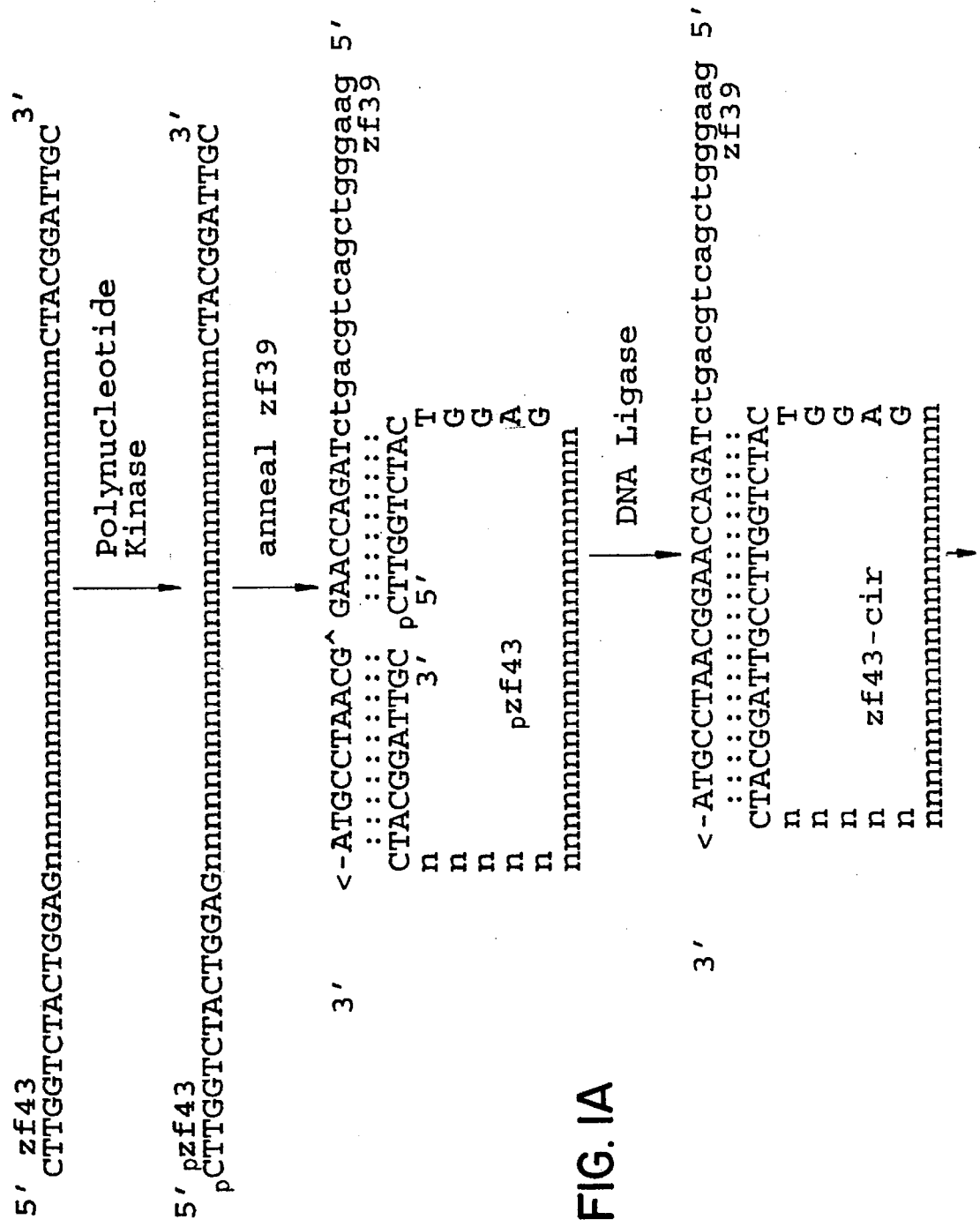
FIG. IA

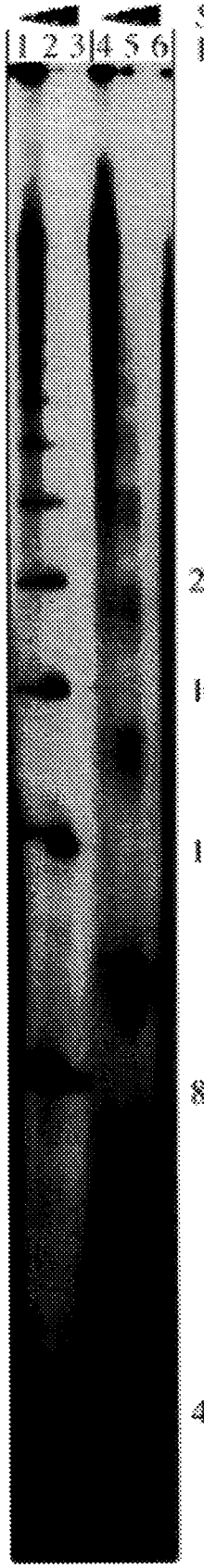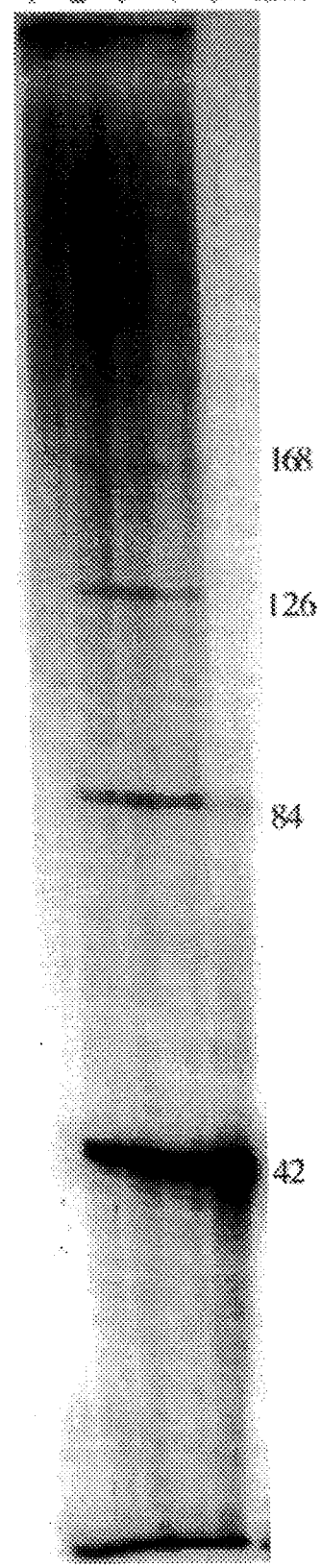
FIG. 3
FIG. 4

FIG. 5A

| clone | structure | repeat units(s) |
|---|---|---|
| SEQ ID NO:4 | | zf43 complement=GCAATCCGTAG(N)26CTCCAGTAGACCAAG |
| SEQ ID NO:5 | pPD74.33 →←→← | 1=GCAATCCGTAGAGGTGAAATCACACCTGATACTAGCCCTCCAG-AGACCAAG |
| SEQ ID NO:6 | pPD74.34 →←→← | 1=GCAATCCGTAGAATGTATATCTTCCGACGTTCT---CTCCAG-AGACCAAG |
| SEQ ID NO:7 | pPD74.36 →←→← | 1=GCAATCCGTAGCTAAGAGGTATCAAACGGTGACTCGGCTCCAGTAGACCAAG |
| SEQ ID NO:8 | | zf42 complement=GCAATCCGTAG(N)16 CTCCAGTAGACCAAG |
| SEQ ID NO:9 | pPD74.21 →←→←→← | 1=GCAATCCGTAGGTTGAGCTCATAACAACTCCAGTAGACCAAG |

FIG. 5B

```
SEQ ID NO:10 pPD74.20    1=GCAATCCGTAGCTAATTGTATGACGG-CTCCAGTAGACCAAG

SEQ ID NO:11 pPD74.09    1=GCAATCCGTAGCCAGGCCTATCTGTGTCCTCCAGTAGACCAAG

SEQ ID NO:12 pPD74.24    1=GCAATCCGTAGAGTATTTAATTAGAACCTCCAGTAGACCAAG

SEQ ID NO:13 pPD74.29    1=GCAATCCGTAGTTCCAAGTTTGAGTTTCTCCAGTAGACCAAG

SEQ ID NO:14 pPD74.23    1=GCAATCCGTAGAGAACACTAATGCCAACTCCAGTAGACCAAG

SEQ ID NO:15 pPD74.30    1=GCAATCCGTAGGACGTAATCTGAAATCCTCCAGTAGACCAAG
```

FIG. 6

| SEQ ID NO: | | | Sequence |
|---|---|---|---|
| SEQ ID NO:16 | pPD74.15 | 1= | GCAATCCGTAGGATGTTCTTATACAC-CTCCAGTAGACCAAG |
| SEQ ID NO:17 | | 2= | GCAATCCGTAGCGTTATAATTGACCACCTCCAGTAGACCAAG |
| SEQ ID NO:18 | pPD74.14 | 1= | GCAATCCGTAGAATGTGAAAATAATCTCTCCAGTAGACCAAG |
| SEQ ID NO:19 | | 2= | GCAATCCGTAGGGGGTGGC------CTCCAGTAGACCAAG |
| SEQ ID NO:20 | pPD74.10 | 1= | GCAATCCGTAGTCTAACTCTAG------CCAGTAGACCAAG |
| SEQ ID NO:21 | | 2= | GCAATCCGTAGCCCGCACGAGTCTCTACTCCAGTAGACCAAG |
| SEQ ID NO:22 | pPD74.19 | 1= | GCAATCCGTAG-----------CTCCAGTAGACCAAG |
| SEQ ID NO:23 | | 2= | GCAATCCGT-GCCAGTGAGTAACCATCCTCCAGTAGACCAAG |
| SEQ ID NO:24 | pPD74.26 | 1= | GCAATCCGTAGACAGATCCGACCCGGCTCCAGTAGACCAAG |
| SEQ ID NO:25 | | 2= | GCAATCCGTAGTATGCCCAGTACCTGCTCCAGTAGACCAAG |
| SEQ ID NO:26 | pPD74.31 | 1= | GCAATCCGTAGCCTTTGTTTCGGCAGCTCCAGTAGACCAAG |
| SEQ ID NO:27 | | 2= | GCAATCCGTAGGACGTCGAGCAGCCCCTCCAGTAGACCAAG |

FIG.7

SEQ ID NO:28  pPD74.12  1+=GCAATCCGTAGACCCTCGACGACCTCCCTCCAGTAGAC+27bp from zf39

SEQ ID NO:29  pPD74.25  1=GCAATCCGTAGCACTGGAACTCCCTCCTCCAGTAGACCAAG

SEQ ID NO:30             2=GCAATCCGTAGACGAAGTGTTCGACC-CTCCAGTAGACCAAG

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CTTGGTCTAC TGGAGCTACG GATTGC 26

( 2 ) INFORMATION FOR SEQ ID NO:2:

(i) SEQUENCE CHARACTERISTICS:
    (A) LENGTH: 37 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:2:

GAAGGGTCGA CTGCAGTCTA GACCAAGGCA ATCCGTA                                    37

(2) INFORMATION FOR SEQ ID NO:3:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:3:

CTTGGTCTAC TGGAGCTACG GATTGC                                                26

(2) INFORMATION FOR SEQ ID NO:4:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:4:

GCAATCCGTA GCTCCAGTAG ACCAAG                                                26

(2) INFORMATION FOR SEQ ID NO:5:

(i) SEQUENCE CHARACTERISTICS:
    (A) LENGTH: 51 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:5:

GCAATCCGTA GAGGTGAAAT CACACCTGAT ACTAGCCCTC CAGAGACCAA G                    51

(2) INFORMATION FOR SEQ ID NO:6:

(i) SEQUENCE CHARACTERISTICS:
    (A) LENGTH: 48 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:6:

GCAATCCGTA GAATGTATAT CTTCCCGACG TTCTCTCCAG AGACCAAG                        48

(2) INFORMATION FOR SEQ ID NO:7:

(i) SEQUENCE CHARACTERISTICS:
    (A) LENGTH: 52 base pairs
    (B) TYPE: nucleic acid
    (C) STRANDEDNESS: single
    (D) TOPOLOGY: linear ( i i ) MOLECULE TYPE: DNA (genomic)

( x i ) SEQUENCE DESCRIPTION: SEQ ID NO:7:

GCAATCCGTA GCTAAGAGGT ATCAAACGGT GACTCGGCTC CAGTAGACCA AG    52

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GCAATCCGTA GCTCCAGTAG ACCAAG    26

( 2 ) INFORMATION FOR SEQ ID NO:9:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GCAATCCGTA GGTTGAGCTC ATAACAACTC CAGTAGACCA AG    42

( 2 ) INFORMATION FOR SEQ ID NO:10:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GCAATCCGTA GCTAATTGTA TGACGGCTCC AGTAGACCAA G    41

( 2 ) INFORMATION FOR SEQ ID NO:11:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GCAATCCGTA GCCAGGCCTA TCTGTGTCCT CCAGTAGACC AAG    43

( 2 ) INFORMATION FOR SEQ ID NO:12:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GCAATCCGTA GAGTATTTAA TTAGAACCTC CAGTAGACCA AG        42

( 2 ) INFORMATION FOR SEQ ID NO:13:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GCAATCCGTA GTTCCAAGTT TGAGTTTCTC CAGTAGACCA AG        42

( 2 ) INFORMATION FOR SEQ ID NO:14:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GCAATCCGTA GAGAACACTA ATGCCAACTC CAGTAGACCA AG        42

( 2 ) INFORMATION FOR SEQ ID NO:15:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GCAATCCGTA GGACGTAATC TGAAATCCTC CAGTAGACCA AG        42

( 2 ) INFORMATION FOR SEQ ID NO:16:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GCAATCCGTA GGATGTTCTT ATACACCTCC AGTAGACCAA G         41

( 2 ) INFORMATION FOR SEQ ID NO:17:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GCAATCCGTA GCGTTATAAT TGACCACCTC CAGTAGACCA AG        42

( 2 ) INFORMATION FOR SEQ ID NO:18:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:18:

```
GCAATCCGTA GAATGTGAAA ATAATCTCTC CAGTAGACCA AG                42
```

( 2 ) INFORMATION FOR SEQ ID NO:19:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

```
GCAATCCGTA GGGGGTGGCC TCCAGTAGAC CAAG                         34
```

( 2 ) INFORMATION FOR SEQ ID NO:20:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

```
GCAATCCGTA GTCTAACTCT AGCTCCAGTA GACCAAG                      37
```

( 2 ) INFORMATION FOR SEQ ID NO:21:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

```
GCAATCCGTA GCCCGCACGA GTCTCTACTC CAGTAGACCA AG                42
```

( 2 ) INFORMATION FOR SEQ ID NO:22:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
GCAATCCGTA GCTCCAGTAG ACCAAG                                  26
```

( 2 ) INFORMATION FOR SEQ ID NO:23:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:23:

GCAATCCGTG CCAGTGAGTA ACCATCCTCC AGTAGACCAA G    41

(2) INFORMATION FOR SEQ ID NO:24:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:24:

GCAATCCGTA GACAGGATCC GACCCGGCTC CAGTAGACCA AG    42

(2) INFORMATION FOR SEQ ID NO:25:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:25:

GCAATCCGTA GTATGCCCAG GTACCTGCTC CAGTAGACCA AG    42

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:26:

GCAATCCGTA GCCTTTTGTT TCGGCAGCTC CAGTAGACCA AG    42

(2) INFORMATION FOR SEQ ID NO:27:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:27:

GCAATCCGTA GGACGTCGAG CAGCCCCTC CAGTAGACCA AG    42

(2) INFORMATION FOR SEQ ID NO:28:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:28:

GCAATCCGTA GACCCTCGAC GACCTCCCTC CAGTAGAC    38

( 2 ) INFORMATION FOR SEQ ID NO:29:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GCAATCCGTA GCACTGGAAC TCCCTCCTC CAGTAGACCA AG    42

( 2 ) INFORMATION FOR SEQ ID NO:30:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

GCAATCCGTA GACGAAGTGT TCGACCCTCC AGTAGACCAA G    41

METHOD FOR CONSTRUCTING AN OLIGONUCLEOTIDE CONCATAMER LIBRARY BY ROLLING CIRCLE REPLICATION

This invention was made with Government support under Contract No. NIGMS 37706 from the National Institutes of Health. The Government may have certain rights in this invention.

BACKGROUND OF THE INVENTION

1. Field of the Invention

This invention relates to a method for constructing oligonucleotide concatamer libraries by rolling circle replication of a single-stranded oligonucleotide. An oligonucleotide concatamer is defined herein as the structure formed by concatenation of unit-sized oligonucleotide components. Concatenation is the process of linking multiple subunits into a tandem series or chain, as occurs during replication of genomic subunits of phage lambda.

Natural genes and proteins often contain tandemly repeated sequence motifs that dramatically increase physiological specificity and activity. Given the selective values of such repeats, it is likely that several different mechanisms have been responsible for their generation. One mechanism that has been shown to generate relatively long tandem repeats (in the kilobase range) is rolling circle replication. In this patent application, we demonstrate that rolling circle synthesis in a simply enzymatic system can produce tandem repeats of monomers as short as 34 bp. These observations provide a facile means for constructing libraries of repeated motifs for use in "in vitro evolution" experiments designed to select molecules with defined biological or chemical properties.

2. Description of the Related Art

Analysis of naturally occurring macromolecular sequences has revealed repetitive structure at a variety of levels (1, 2). Particularly relevant to gene expression and replication are sets of short sequence motifs that often occur in multiple copies around promoter/enhancer regions and replication origins (3). The repetition of motifs within a control region has been shown in many cases to allow individual trans-acting factors to exert additive and/or cooperative effects; this design can improve the specificity of a control mechanism by increasing the signal of appropriate activity while decreasing the possibility of fortuitous inappropriate activity (4). Requirements for repeated sequence motifs have also been found in characterizing the activities of specific RNA (5-8) and protein (9-11) functions.

In investigating structure-function relationships in vitro and in vivo, several researchers have used strategies that involve the production of a large library of random sequences followed by selection for sequences with a given property (12). These schemes can produce experimentally useful reagents and provide a wealth of information about sequence requirements for the selected activity (e.g., refs. 13-15). Application of such a selection strategy depends on the ability to produce large libraries of random sequences, efficient selection procedures, and appropriate means for recovering and characterizing the selected molecules. Frequently, the techniques for selection or screen of molecules are insufficient to find active sequences. In particular, if several tandem copies of a functional segment are required for activity, then the problem of recovering an active sequence from a random pool becomes increasingly more difficult.

To circumvent the insufficiency of available selection techniques for many interesting biological and biochemical activities, we sought to produce libraries of random repeated sequences: pools of molecules in which each member contains tandem repeats of a different sequence element. The potential usefulness of such concatamer libraries can be illustrated by calculating the probability that a given 8-base pair element will occur independently in three positions in a single random 60-mer sequence ($\approx$1 in 250 million). If we replace the random 60-mers with a library of trimerized random 20-mers, then this probability improves by $\approx$5 orders of magnitude.

We considered several different methods for constructing concatamer libraries. Chemical synthesis can be used to generate random pools of DNA sequence oligomers (12), but straightforward ligation to concatenate elements from these pools would not produce the desired result, since there is no means to ensure that ligation joins molecules of the same sequence. A straightforward method for generation of a small library would be to separately synthesize and concatenate a number of separate oligonucleotides (16); unfortunately, this would be cumbersome and expensive for large libraries.

As a more general procedure we chose a scheme based on the rolling circle replication used by many plasmids and viruses (17, 18). Rolling circle replication is a mode of replication in which a replication fork proceeds around a circular template for an indefinite number of revolutions. The nucleic acid strand newly synthesized in each revolution displaces the strand synthesized in the previous revolution, giving a tail containing a linear series of sequences complementary to the circular template strand.

Rolling circle replication involves two simultaneous processes: (i) DNA polymerase must synthesize sequences complementary to a circular template. (ii) As this replication proceeds, some mechanism must unwind the parental duplex to allow the polymerase to advance. Models for physiological rolling circle replication generally involve a template that is predominantly double stranded, with a helicase or single-strand DNA binding activity preceding the polymerase to allow replication to continue (17, 18). Characterized rolling circle replication mechanisms have been found to operate on templates on the order of kilobases and larger (18). Rolling circle replication of templates smaller than 100 bp by previously described mechanisms would be considered unlikely, since formulation of very short double-stranded circles would be topologically obstructed (19). Although there was no precedent, we chose to examine the ability of predominantly single-stranded circles to act as templates for rolling circles synthesis.

SUMMARY OF THE INVENTION

The present invention discloses a four-step in vitro method for constructing an oligonucleotide concatamer library. The first step involves the generation of a primer-bridged circular template oligonucleotide by annealing a linear primer oligonucleotide to a complementary linear template oligonucleotide and ligating the linear template oligonucleotide into a circular template oligonucleotide. The second step involves the generation of a single-stranded oligonucleotide concatamer by rolling circle replication of the circular oligonucleotide template. In the third step, the single-stranded oligonucleotide concatamer is converted to a double-stranded oligonucleotide concatamer. Finally, the double-stranded oligonucleotide concatamer is cloned or used directly in in vitro selection systems.

More specifically, the primer-bridged circular template oligonucleotide is generated by producing a linear single-stranded template oligonucleotide having a phosphorylated 5' end and a complementary single-stranded primer oligonucleotide, i.e., a primer oligonucleotide with permuted complementarity to the linear single-stranded template oligonucleotide. The linear single-stranded primer oligonucleotide is then annealed to the complementary linear single-stranded oligonucleotide primer. In the annealing, the 3' and 5' ends of the linear single-stranded template oligonucleotide are bridged together into a circle using the complementary primer oligonucleotide. The circle is made covalent by ligating the 3' and 5' ends of the linear single-stranded template oligonucleotide to form the primer-bridged circular template oligonucleotide.

The circularized primer-template oligonucleotide is reacted with nucleic acid polymerase in the presence of nucleoside triphosphates to form the single-stranded oligonucleotide concatamer.

The single-stranded oligonucleotide concatamer is then converted to a double-stranded oligonucleotide concatamer by reacting the single-stranded oligonucleotide concatamer with nucleic acid polymerase in the presence of nucleoside triphosphates to form the double-stranded oligonucleotide concatamer.

Finally, the double-stranded oligonucleotide concatamer is cloned by inserting the double-stranded oligonucleotide concatamer into a plasmid vector and transforming a host cell with the plasmid vector. Alternatively, the double-stranded oligonucleotide concatamer can be assayed directly for biological activity in an in vitro assay system that permits isolation or amplification of active molecules.

BRIEF DESCRIPTION OF THE DRAWINGS

FIG. 3 shows the partial digestion of reaction products with restriction enzyme Sty I. As above, samples were denatured and resolved on sequencing-type gels. Lanes: 1–3, digestion of zf42 extension product; 4–6, identical except that the template has been derived from oligonucleotide zf43, which is longer than zf42 by 10 bases. The broadened bands observed in lanes 4–6 apparently result from the presence of shorter (internally deleted) oligonucleotide molecules in the zf43 preparation.

FIG. 4 shows the full digestion of reaction products with Sty I. Lanes: 1, undigested products from a 4-hr extension using zf42 as template; 2–5, digestion with concentrations of Sty I in a range expected to yield full digestion. The major band at 42 nt presumably represents completely digested unit-length material (the doublet band may represent the two different product strands). A small amount of material migrating at 84 bp with the highest Sty I concentration is likely to result from a residual level of incomplete level of incomplete digestion. Other (minor) bands have not been characterized.

FIGS. 5–7 depict the structures of 18 clones from E. coli DNA polymerase I extension of primer-templates. Sequences of DNA from 18 arbitrarily chosen clones from putative rolling circle synthesis are shown. Plasmids pPD74.33, –74.34, and –74.36 were derived from zf43; all others were derived from zf42. In three cases (pPD74.19, –74.21, and –74.23), the plasmids analyzed apparently contained two different inserts that had been joined during ligation of insert to plasmid vector; in these cases, only the first insert is described.

FIG. 5 shows the ten "simple" products each had the structure predicted for rolling circle synthesis from the input primer-template. In several cases, the periodic repeat in these products differs in size by 1–4 bp from the design of the input oligonucleotide; this probably reflects a population of internally deleted oligonucleotides in 10 the original zf42 and zf43 preparations.

FIG. 6 shows that six products had an alternating pattern derived from two different input molecules. These are assumed to result from formation of dimeric primer-template circles in the initial ligation (two input molecules joined end to end to end). Consistent with this hypothesis, when the initial ligation to form zf42 circles was performed at a 10-fold higher concentration of template and primer, a majority of clones (70%) exhibited an alternating structure.

FIG. 7 shows that two products had structures that were not simply explained, although each had a repeated structure consistent with a rolling circle event.

DETAILED DESCRIPTION OF THE INVENTION

Figure 1B:
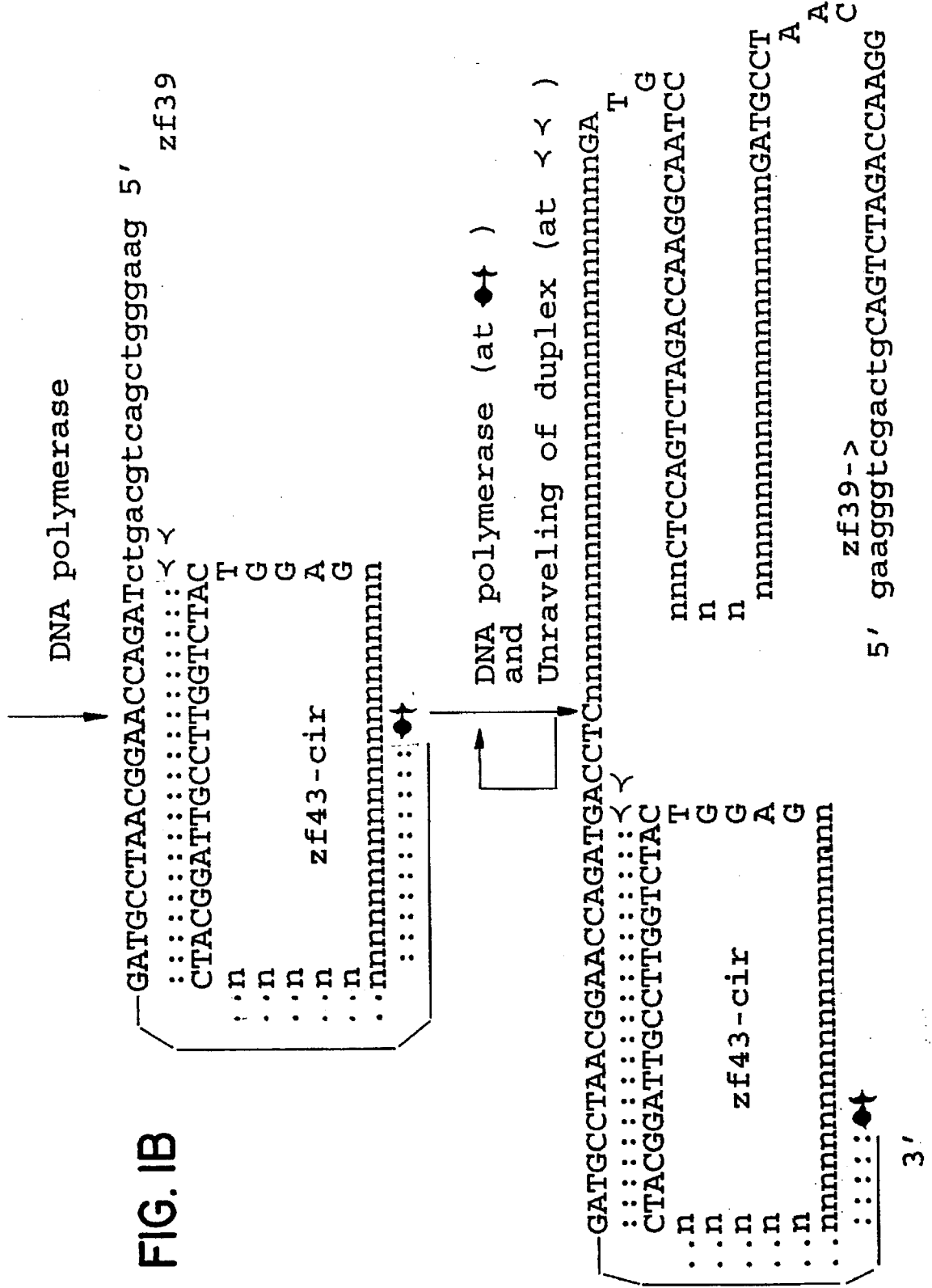
FIG. 1 demonstrates the method of the present invention for generation of a concatamer library using rolling circle replication. The template oligonucleotide, zf43 (SEQ ID NO:1), is circularized by bridging with a partially complementary oligonucleotide, zf39 (SEQ ID NO:2), as a guide. This primer-bridged template then reacts with DNA polymerase in the presence of deoxynucleoside triphosphate precursors. As synthesis proceeds, the polymerase creates duplex DNA. At some point, the circle becomes constrained so tightly that polymerization cannot proceed without some relief of the restraint. One possible outcome is shown: the constraint on the small circle might drive unwinding at the lagging end of the duplex. If this process is combined with continued polymerization, then a long repeating polymer would be produced. For this figure, the 52-based oligonucleotide, zf43 (SEQ ID NO:1), is shown as template; oligonucleotide zf42 (SEQ ID NO:3), used in other experiments, is identical in the constrained regions but has 10 fewer nonspecified residues (total length, 42 bases). Any template oligonucleotide could be used provided that a suitable primer oligonucleotide is produced to guide circularization.

The method of the present invention for generation of a concatamer library using rolling circle replication is shown in FIG. 1. The experimental design demonstrated in FIG. 1 was based on a consideration of possible behavior for a primer oligonucleotide that is being extended by DNA polymerase after annealing to a single-strand circular template. As the primer is extended, a double-stranded region of the circle will be formed. At a certain point, this double-stranded region will become sufficiently long to "strain" the circular topology. At this point, one of three events might occur: (i) the polymerase might stall or stop; (ii) the template might be forced to unravel behind the polymerase; or (iii) unwinding might occur at the site of polymerization-this could lead to self-priming of the product strand (20).

If unraveling behind the polymerase occurs, then a rolling circle mechanism could be set up; the production of new double-stranded regions as the polymerase progresses 5' to 3' would provide a stearic force unwinding the DNA duplex behind the active polymerase. Under these circumstances, the energy for both polymerization and helicase activity would be derived from utilization by DNA polymerase of nucleoside triphosphates.

The substrates we used to test this rolling circle replication scheme are shown in FIG. 1. A primer template pair is set up by using two oligonucleotides with a permuted region of complementarity. Annealing and ligation of these two oligonucleotides should produce a primed, partially single-stranded circle. To provide diversity in the template population, most of the unpaired residues are nonspecified (i.e., an equimolar mixture of A, G, C, and T). Rolling circle synthesis should then generate a population of long single-stranded products, each containing repeats complementary to an individual template molecule.

Figure 2:
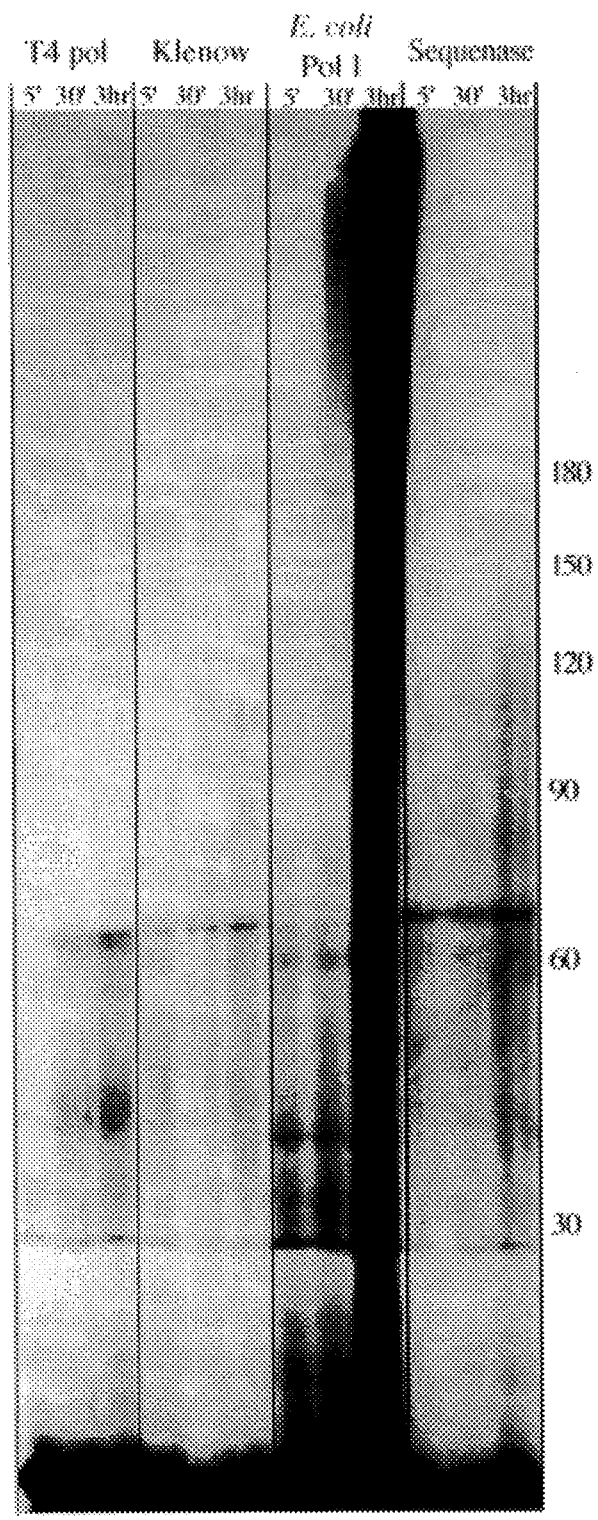
FIG. 2 shows the time course of extension reactions for the electrophoretic separation of reaction products. The annealed primer-template diagrammed in FIG. 1 was extended with the indicated polymerase in the presence of [$^{32}$P]dCTP. At the indicated time points, aliquots were removed, denatured, and resolved on a sequencing-type gel. Base numbers on the right sizes deduced from standard DNA sequencing reactions run on the same gel. A delayed time course in the synthesis reaction with E. coli polymerase I (Pol I) (compare 30-min and 3-hr samples) has been seen with a variety of primer-template combinations and polymerase preparations.

In initial experiments with several available DNA polymerase enzymes, we found that *E. coli* DNA polymerase I was particularly efficient in synthesizing high molecular weight products from the primer template; after 3 hr, a large amount of high molecular weight product had formed (FIG. 2).

After conversion to a double-stranded product, the material was further characterized by partial restriction digestion, with an enzyme cutting once in each repeat. The resulting ladder of bands (FIG. 3) was consistent with a tandem array structure derived from rolling circle synthesis. As expected, more complete digestion with the restriction enzyme (FIG. 4) produced material that was predominantly monomer length. An estimate of the yield from a 4-hr extension with *E. coli* polymerase I was obtained from these experiments: ≈15 ng of Sty I-sensitive high molecule weight material was synthesized per pmol of input oligonucleotides.

As a critical test of the rolling circle model, it was essential to show that the reaction indeed produced repeats derived from individual input templates. This was demonstrated by cloning and sequencing of reaction products. Since the original oligonucleotides contained 16 (or 26) nonspecified basis, repetition of the identical sequence in several consecutive members of a concatamer would be conclusive evidence that the cloned multimer is indeed derived by a replication event from a single template molecule.

From one set of synthesis reactions, we sequenced 18 different cloned products (FIGS. 5–7). All gave different sequences. Ten of these sequences had the predicted structures, with each having 3–5 tandem copies of a unique oligonucleotide from the original pool (FIG. 5). Six of the characterized clones had an alternating structure in which two of the initial oligonucleotides alternate in a mixed tandem array (FIG. 6). These products could result from dimer circles (bridged by two primer molecules) formed during annealing and ligation of the initial primer template. The remaining two clones had repeated structures that require more complex explanations but nonetheless evidence the occurrence of rolling circle replication events (FIG. 7).

Using other templates similar to those shown in FIG. 1, we have observed replication products with tandem repeats of monomers as short as 34 bp. In these and previous experiments, there has been no indication of specific sequence requirements for rolling circle synthesis. In particular, examination of the recovered sequences from FIGS. 5–7 reveal no evidence for bias in either base composition or secondary structure.

The following examples are used to more specifically describe the present invention. The following reagents and procedures were used in Examples 1–4. Oligonucleotides were made on an Applied Biosystems DNA synthesizer (model 380B), desalted, precipitated with ethanol, and used without further purification. Bacteriophage T4 DNA ligase, polynucleotide kinase, and DNA polymerase were from New England Biolabs. *Escherichia coli* DNA polymerase was from Bethesda Research Laboratories; DNA polymerase large fragment (Klenow) and Sty I were from Boehringer Mannheim. Modified phage T7 DNA polymerase (Sequenase) was from United States Biochemical.

EXAMPLE 1

Specific protocol for step 1 formation of the primer-bridged template using oligonucleotides zf42 and zf43 as template and oligonucleotide zf39 as primer.

Primer-bridged template was produced by dilute annealing followed by ligation. Template oligonucleotide (zf42 of zf43) (0.8 nmol) was phosphorylated with T4 polynucleotide kinase (60 Richardson units) in 250 µl of LK buffer (50 nM Tris.HCl, pH 7.8/10 nM $MgCl_2$/10 mM dithiothreitol/1 mM ATP/25 µg of bovine serum albumin per ml). After heating to 70° C. for 10 min, the material was immediately diluted at 37° C. into 12 ml of LK buffer containing 0.7 nmol of primer oligonucleotide (zf39). After 30 min at 23° C., the sample was transferred to 16° C. and incubated for 4 hr with T4 DNA ligase (120 Weiss units). Ligase reactions were stopped by addition of EDTA (to 10 mM), SDS (to 0.1%), $NH_4OAc$ (to 1M), and 50 µg of glycogen, extracted once each with 8 ml of phenol/chloroform (1:1) and chloroform and precipitated twice with ethanol. Final samples were resuspended in 25 µl of TEN (10 mM Tris.HCl, pH 7.5/1 mM EDTA/25 mM NaCl) and stored at −70° C. In handling the annealed primer-template, care was taken to avoid transient low-salt or high-temperature conditions that could lead to denaturation.

EXAMPLE 2

Specific protocol for step 2 primer extension reactions using zf39 primer-bridged templates described in Example 1.

Primer extension reactions were carried out in 20 µl with 0.8 µl of primer-template. Extension reaction mixtures contained 10 mM Bistris propane chloride; 10 mM NaCl; 1 mM dithiothreitol; 1 mM each dATP, dTTP, dGTP; 0.25 mM dCTP (including [$^{32}$P]dCTP to a specific activity of 0.5 Ci/mmol; 1 Ci=37 (giga Becquerel or GBq); 0.1 mg of bovine serum albumin per ml; and the indicated polymerase (in some experiments 50 mM NaCl was added; this did not change the product electrophoresis pattern). Incubations were at 23° C. for T4 and Klenow, large fragment of *E. coli* DNA polymerase I (18), and 37° C. for *E. coli* DNA polymerase I and coliphage T7 DNA polymerase (Sequenase).

Although *E. coli* DNA polymerase was most efficient under the reaction conditions used, longer exposures revealed similar patterns for Klenow and T7; we have not extensively varied reaction conditions to optimize output with these enzymes. Similar reactions with thermophilic DNA polymerases (Vent, Pfu, and Taq; reactions at 58° C.) produced no detectable rolling circle products but instead produced a series of products indicative of multiround rolling hairpin replication as described by Cavalier-Smith (20) (although we cannot rule out the possibility that some

EXAMPLE 3

Specific protocol for step 3 formation of double-stranded oligonucleotide concatamer.

For further characterization by restriction digestion and cloning, we used material from 4-hr extension products produced with E. coli DNA polymerase I. This analysis required that the product be converted to a double-stranded form. In initial experiments, an extra round of DNA synthesis was performed to produce the second strand. This was done by isolating the reaction product and allowing self-priming in a standard hairpin reaction (20). Subsequently, we found that much of the product was double stranded even without this second round of synthesis. A plausible explanation would be that self-priming hairpin structures (20) form at some frequency during the initial 4-hr synthesis reaction, perhaps after unraveling of the link between the elongating DNA terminus and the rolling circle template.

Partial digestion was carried out with restriction endonuclease Sty I, which should cut just once in each tandem repeat. To check the efficiency of the partial digest, samples were resolved after denaturation on a 6% acrylamide sequencing gel. Preparative samples were resolved in parallel without denaturation; these produced a shifted ladder of bands consistent with the double-stranded character of the material.

EXAMPLE 4

Specific protocol for step 4 cloning of digested rolling circle material into a double-stranded plasmid vector.

The nondenatured samples from the Sty I partial digest were excised, eluted, ligated into a suitable Sty I-cut bacterial plasmid vector and transformed into a Rec⁻ bacterial host. The plasmid used was vector pPD18.56, to which a Sty I site had been added by oligonucleotide insertion (23). The Rec⁻ bacterial host used was DH5α (24). Production of cloned libraries from the partial digest material was relatively efficient; by using standard protocols for bacterial transformation ($10^6$ colonies per µg of control plasmid DNA), several hundred clones were obtained with material derived from 1 pmol of input oligonucleotides. Much larger libraries could readily be obtained by optimizing and scaling up the bacterial transformation.

We have shown that E. coli DNA polymerase I is capable of carrying out a rolling circle type synthesis reaction on a very short circular template. Although the mechanism of this reaction has not been studied in detail, several theoretical considerations of topology and scale are relevant. First, the short templates used in these experiments would be unlikely to form fully double-stranded circuits without extreme topological strain.

As an alternative, it seems likely that the replicating complex consists of a predominantly single-stranded circle, with DNA polymerase working to extend a short double-stranded region. At a certain point, extending the total length of the double-stranded region would be energetically unfavorable. At this point, continued polymerase activity (at the leading end) could drive unwinding behind the polymerase. A second constraint comes from a requirement for rotational positioning of DNA polymerase on the template. The twist in the local DNA helix at the site of synthesis necessitates a rotation of polymerase relative to template. This must occur without the polymerase physically passing through the cyclized DNA template. DNA polymerase I is sufficiently large (from the Klenow crystal structure; see ref. 21) that even with maximum contortion, a nucleotide chain of less than 60 residues could not encircle it.

As an alternative, polymerase could act essentially as a fixed surface while the template continually twists inward on itself. The combined forward and twisting motion of the template could provide the necessary constant interface between polymerase and template.

The ability of isolated polymerase to carry out rolling circle synthesis on a small DNA circle in vitro suggests that this process could have played an evolutionary role, along with mechanisms such as unequal recombination, transposition, and replication slippage (2, 18), in generating the plethora of natural tandem-repeat structures that appear in coding and noncoding sequences.

The enzymatic activities used in our scheme (kinase, ligase, and DNA polymerase) are readily available in vivo. Template oligonucleotides might come from a pool of replication intermediates or nucleic acid breakdown products present in cells.

The final requirement (permuted complementary between primer and template oligonucleotides) would be a relatively rare coincidence; nevertheless, even a small genome would be expected statistically to contain many suitable combinations of sequences.

Given the efficiency of the in vitro reaction, it is conceivable that short circles might replicate in vivo as part of a concerted physiological or pathological process. The smallest known circular replicons are small viroid and satellite virus RNAs of several hundred base pairs (22). It is conceivable that there are (as yet undiscovered) shorter plasmids or viroid-like parasites that replicate by using the single-stranded rolling circle mechanism described here.

We have already begun using these concatamer libraries to characterize cis-acting control sequences with defined activation patterns, with the goal of identifying the corresponding developmentally regulated transcription factors. Three other potential uses for concatamer libraries are notable.

(i) Vergnaud et al. (16) have used individually synthesized and concatamerized random oligonucleotides as hybridization probes to identify human DNA polymorphisms. The ability to make large libraries of random concatamers should greatly facilitate this approach.

(ii) In a variety of systems, sequences controlling translation have been localized to short repeated sequence motifs in the 3' nontranslated leader of the mRNA (5–8). By constructing a library of concatamers inserted into the 3' leader sequence for an easily assayed reporter gene/expression vector, it would be possible to identify control sequences producing different patterns of translational regulation.

(iii) Repeated motifs in proteins have been used in evolution to produce tight and very specific protein-protein interactions (9–11). Construction of a concatamer library in a protein coding context should allow in vitro or in vivo selection of repeated peptide sequence motifs that allow specific binding to a target protein.

Many of these selective schemes could be envisioned as a two-step process. Once a molecule with desired characteristics has been identified in any of the above screens, a second round of selection could be carried out to isolate sequences with optimal activity. This would only be done by starting with material in which each base is only partially randomized relative to the initially recovered active sequence (e.g., an A residue in the initial selected sequence might be replaced by a mixture of 90% A+5% G+3% T+2% C).

From an experimental point of view, the ability to produce large libraries of random or semirandom concatamers should have numerous applications. The rolling circle library technique described in this patent application should facilitate discovery and development of novel compounds for pharmaceutical, diagnostic, and other medical and chemical applications.

A variety of methods currently in use for discovery and development rely on the ability to select molecules with a desired property from a large (and partially or completely random) population. Application of such a selection strategy depends on the ability to produce large libraries of random sequences, on efficient selection procedures, and on appropriate means for recovering (and amplifying) selected molecules.

Frequently, the techniques for selection or screening of molecules are insufficient to find active sequences. In particular, if (as often occurs in natural systems) several tandem copies of a functional segment are required for activity, then the probability of finding an active sequence, even in a large random pool, becomes vanishly small. The methods described in this application allow such tandem sequences to be produced at frequencies which will permit many such screens to proceed.

The following examples will serve to exemplify the general applicability of the present invention in regard to DNA elements (Example 5), RNA elements (Example 6), and protein elements (Example 7).

EXAMPLE 5

DNA elements.

By incorporating rolling circle material into DNA shuttle vectors designed to follow gene expression, a given cell type can be used to select out enhancer sequences which optimize expression, maximize replication or allow response to a specific stimulus. This approach is particularly suited to the concatamer libraries, given the repetitive structure seen both in natural enhancers and optimal enhancers constructed in vitro.

EXAMPLE 6

RNA elements.

As with DNA elements in Example 5, it will be possible to select out elements (either in vitro or in vivo) which can impart specific regulatory or catalytic properties to an RNA molecule. These properties include improved translation, improved function as antisense or ribozyme inhibitors, or ability of the RNA to respond (by translation or degradation) to specific environmental conditions.

EXAMPLE 7

Protein elements.

The use of the present invention with protein elements will provide for the most varied and powerful applications. Rolling circle material, e.g. DNA, can be inserted into a protein expression vector, to allow the screening of random concatamers of amino acid sequences for biological function. In particular, the goal of these selections will be to obtain relatively small repetitive peptides that could be useful either as diagnostic agents (by virtue of specifically selected binding activities), or as therapeutic agents (by selecting or appending molecules that interfere with or stimulate activity of their targets). The activities that could be sought are limited only by the availability of activity assays. Exemplary targets for these screens include (1) viral and bacterial surface proteins or their cellular receptors; (2) specific components of non-desirable cells such as parasites and tumor cells; (3) receptors involved in tissue growth or regeneration; and (4) essential molecules in insect and non-insect pests.

The following examples will serve to exemplify the specific applicability of the present invention in regard to a diagnostic application (Example 8), and a pharmacological application (Example 9). Each example for concatamer libraries entails the following:

a) a desired biological activity and b) means for selecting or amplifying molecules which produce the desired activity.

In each case, we will explain the advantages that a concatamer library would have as a starting material in obtaining a high-affinity/high-activity reagent.

EXAMPLE 8

Exemplary diagnostic application.

a) Desired activity: Tight and selective binding to a specific pathogen (e.g. virus or bacterium). This would provide a potential diagnostic reagent for sensitive detection of the pathogen in medical or other samples.

b) Means for selecting active molecules:

i) A bacterial library expressing randomized concatamers of fixed or variable length is constructed by the methods above. These concatamers are expressed either as RNA transcripts or as translated protein molecules (by cloning the rolling circle material into a plasmid expression vector).

ii) A large number of bacteria containing individual members of the library are grown as individual colonies, transferred to nitrocellulose or nylon filters, and lysed (such procedures are standard procedures in bacterial genetics, analogous techniques using bacteriophage, mammalian cells or yeast expression constructs could likewise be used).

iii) The pathogen to be detected is isolated in bulk, labelled with fluorescent or radioactive tracer, and bound to the filters. Colonies or phage plaques exhibiting binding are further characterized by examining specificity with a variety of related but distinct probes (e.g. other viral or bacterial strains).

Advantages of a concatamer library in obtaining high-affinity reagents: Viruses and bacteria almost invariably have large numbers of identical coat or cell proteins on their surface. By using a population of concatenated RNA or protein molecules as a starting point, the probability of obtaining a molecule which can bind simultaneously to several different surface proteins is maximized. This maximization would have the effect of greatly increasing both affinity and potential discrimination of the isolated reagent.

EXAMPLE 9

Exemplary pharmacological application.

a) Desired activity: Produce a molecule that will act as an agonist or antagonist interacting with a given cellular receptor. In this example, we will assume that a specific growth factor receptor has been isolated, and that there is a need to produce an agonist which functionally activates that receptor. Similar means could be used for any selectable process.

b) Means for selecting active molecules: These schemes start with a tissue culture cell line which is dependent for growth on the activity of the selected growth factor. This cell line is transformed with a library of concatamer sequences expressed in a secreted expression vector (one which produces protein products which will be presented in an autocrine fashion to cell surface receptors). Cell division in the absence of exogenously added growth factor is then selected as the primary screen, with secondary screens for:
  i) dependence on the growth factor receptor and
  ii) biochemical interaction between the selected concatamer and putative receptor.

Advantage of concatamer library: Many growth factors have a repetitive monomer structure, with several tandem copies of similar peptide sequence. In addition, many cellular receptors are multimers of individual polypeptide subunits. In isolating novel molecules with high affinity, these repetitive features would provide significant advantages to schemes starting with a concatamer library. A second consideration relates to the mechanism of activation for many growth factor receptors and other cellular regulatory components that are physiologically activated upon dimerization or higher order multimerization. A concatamer library should provide the ideal type of multisite activation reagent to promote such a dimerization or multimerization reaction.

While the invention has been described in connection with what is presently considered to be the most practical and preferred embodiments, it is to be understood that the invention is not limited to the disclosed embodiments, but on the contrary is intended to cover various modifications and equivalent arrangements within the spirit and scope of the appended claims.

Thus, it is to be understood that variations in the method for constructing a nucleotide concatamer library can be made without departing from the novel aspects of this invention as defined in the claims.

The following publications were cited above and are hereby incorporated by reference and relied upon:

1. Britten, R. J. & Kohne, D. E. (1968) *Science* 161, 529–540.
2. Beridze, T. (1986) *Satellite DNA* (Springer, Berlin).
3. Trifonov, E. N. & Brendel, V. (1986) *Gnomic: A dictionary of Genetic Codes* (Balaban, Rehovot, Israel).
4. Ondek, B., Shepard, A. & Herr, W. (1987) *EMBO J.* 6, 1017–1025.
5. Theil, E. C. (1990) *J. Biol. Chem.* 265, 4771–4774.
6. Wharton, R. P. & Struhl, G. (1991) *Cell* 75, 855–862.
7. Goodwin, E. B., Okkema, P. G., Evans, T. C. & Kimble, J. (1993) *Cell* 75, 329–339.
8. Wightman, B., Ha, L. & Ruvkun, G. (1993) *Cell* 75, 855–862.
9. Corden, J. L. (1990) *Trends Biochem. Sci.* 5, 383–387.
10. Bork, P. (1992) *Biochemistry* 31, 10643–10651.
11. Engel, J. (1992) *FEBS Lett.* 307, 49–54.
12. Szostak, J. (1992) *Biochemistry* 31, 10643–10651.
13. Bartel, D. P. & Szostak, J. W. (1993) *Science* 261, 1411–1418.
14. Beutel, B. A. & Gold, L. (1992) *J. Mol. Biol.* 228, 803–812.
15. Barbas, C. F., Amberg, W., Simoncsits, A., Jones, T. M. & Lerner, R. A. (1993) *Gene* 137, 57–62.
16. Vergnaud, G., Mariat, D., Apiou, F., Aurias, A., Lathrop, M. & Lauthier, V. (1991) *Genomics* 11, 135–144.
17. Gilbert, W. & Dressier, D. (1968) *Cold spring Habor Symp. Quant. Biol.* 33, 473–484.
18. Baker, T. A. & Kornberg, A. (1992) *DNA Replication* (Freeman, N.Y.).
19. Koo, H.-S., Drak, J., Rice, J. A. & Crothers, D. M. (1990) *Biochemistry* 29, 4227–4234.
20. Cavallier-Smith, T. (1974) *Nature* (London) 250, 467–470.
21. Ollis, D. L., Brick, P., Hamlin, R., Xuong, N. G. & Steitz, T. A. (1985) *Nature* (London) 313, 762–7666.
22. Diener, T. O. (1991) *FASEB J.* 5, 2808–2813.
23. Okkena, P., Harrison, S., Plurger, V., Aryana, A. & Fire, A. (1993) *Genetics* 135, 385.
24. Ausubel, F. M., Brent, R., Kingston, R. C., Moore, D. D., Seidman, J. G., Smith, J. A., and Struhl, K. (eds) (1990) *Current Protocols in Molecular Biology*, John Wiley & Sons, New York.

What is claimed is:

1. An in vitro method for constructing an oligonucleotide concatamer library, comprising the steps of:
   a) generating a population of primer-bridged circular template oligonucleotides by annealing linear primer oligonucleotides to linear template oligonucleotides and ligating said linear template oligonucleotides into circular template oligonucleotides;
   b) generating a population of single-stranded oligonucleotide concatamers by rolling circle replication of said primer-bridged circular template oligonucleotides; and
   c) generating a population of corresponding double-stranded oligonucleotide concatamers by synthesizing single stranded oligonucleotides which are complementary to said population of single-stranded oligonucleotide concatamers.

2. The method of claim 1, further comprising the step of:
   d) cloning said double-stranded oligonucleotide concatamers.

3. The method of claim 1, wherein said primer-bridged circular template oligonucleotides are generated by:
   i) producing linear single-stranded template oligonucleotides having a phosphorylated 5' end and a single-stranded primer oligonucleotide with permuted complementarity to said linear single-stranded template oligonucleotides;
   ii) annealing said linear single-stranded primer oligonucleotides to said linear single-stranded template oligonucleotides; and
   iii) ligating said linear single-stranded template oligonucleotides to form primer-bridged circular template oligonucleotides.

4. The method of claim 1, wherein said population of single-stranded oligonucleotide concatamers is generated by reacting said primer-bridged circular template oligonucleotides with nucleic acid polymerase in the presence of nucleoside triphosphates to form single-stranded oligonucleotide concatamers.

5. The method of claim 1, wherein said population of single-stranded oligonucleotide concatamers is converted to a population of double-stranded oligonucleotide concatamers by reacting said population of single-stranded oligonucleotide concatamers with nucleic acid polymerase in the presence of nucleoside triphosphates.

6. The method of claim 2, wherein said population of double-stranded oligonucleotide concatamers is cloned by:
   i) inserting said double-stranded oligonucleotide concatamers into a plasmid vector to obtain a mixture of ligation products; and
   ii) transforming a host cell with said mixture.

7. The method of claim 6, wherein said host cell is a bacterial cell.

8. The method of claim 1, wherein said oligonucleotide concatamer library is a DNA oligonucleotide concatamer library.

9. The method of claim 4, wherein said nucleic acid polymerase is a DNA polymerase.

* * * * *